United States Patent
Beger et al.

(10) Patent No.: US 10,631,841 B2
(45) Date of Patent: Apr. 28, 2020

(54) SURGICAL RETRACTOR SYSTEM COMPRISING A RETRACTOR AND AN EXTRACTOR AS WELL AS A SURGICAL INSTRUMENT APPLYING A TORSIONAL LOAD

(71) Applicant: Aesculap AG, Tuttlingen (DE)

(72) Inventors: Jens Beger, Tuttlingen (DE); Mario Serpa, Tuttlingen (DE); Frank-Markus Storz, Tuttlingen (DE); Francis Kilian, Emmelshausen (DE)

(73) Assignee: Aesculap AG (DE)

( * ) Notice: Subject to any disclaimer, the term of this patent is extended or adjusted under 35 U.S.C. 154(b) by 134 days.

(21) Appl. No.: 15/939,998

(22) Filed: Mar. 29, 2018

(65) Prior Publication Data
US 2018/0280014 A1    Oct. 4, 2018

(30) Foreign Application Priority Data
Mar. 30, 2017   (DE) .................. 10 2017 106 846

(51) Int. Cl.
*A61B 17/02* (2006.01)
(52) U.S. Cl.
CPC ........ *A61B 17/0218* (2013.01); *A61B 17/025* (2013.01); *A61B 2017/0225* (2013.01)
(58) Field of Classification Search
CPC ....... A61B 1/32; A61B 17/02; A61B 17/0218; A61B 17/025; A61B 17/0225; A61F 2/82; A61F 2/86; A61F 2/90
See application file for complete search history.

(56) References Cited

U.S. PATENT DOCUMENTS

| | | | |
|---|---|---|---|
| 6,083,225 A * | 7/2000 | Winslow | A61B 17/025 606/279 |
| 6,582,431 B1 | 6/2003 | Ray | |

(Continued)

FOREIGN PATENT DOCUMENTS

| | | |
|---|---|---|
| DE | 102007025921 A1 | 12/2008 |
| DE | 102012019432 A1 | 4/2014 |

(Continued)

OTHER PUBLICATIONS

Partial European Search Report for European Application No. 18 164 843.7, dated Aug. 10, 2018, with translation, 20 pages.

(Continued)

*Primary Examiner* — Eric S Gibson
(74) *Attorney, Agent, or Firm* — RatnerPrestia

(57) ABSTRACT

A surgical retractor system includes a substantially tubular retractor having several segments which can be irreversibly severed from one another to carry out a length adaptation of the retractor. A segment is subdivided into an expanding section and a plate section of differing radial flexibility and connected to each other in a one-piece material bond to allow plastic radial expansion of the retractor. An extractor can be operated to bring about plastic radial constriction of the retractor contrary to the radial expansion of the retractor. The extractor is prepared to cooperate with the plate section to bring about radial constriction of the retractor. A surgical instrument for removing a distractor or retractor from an opening includes at least one handle section defining a handle's longitudinal axis and at least one operating section defining a longitudinal effective axis, which are coupled to each other by a connecting section.

9 Claims, 4 Drawing Sheets

(56) References Cited

U.S. PATENT DOCUMENTS

Figure 1:
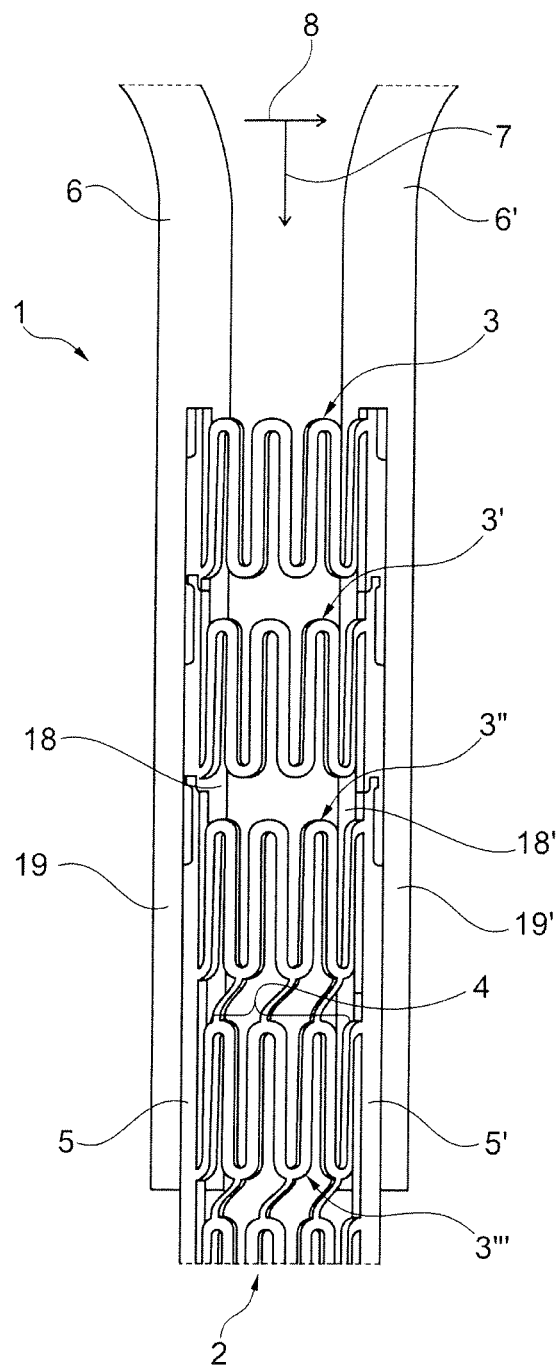

| | | | |
|---|---|---|---|
| 6,821,291 B2 | 11/2004 | Bolea et al. | |
| 2005/0125053 A1 | 6/2005 | Yachia et al. | |
| 2008/0033528 A1 | 2/2008 | Satasiya et al. | |
| 2008/0058606 A1* | 3/2008 | Miles | A61B 1/32 600/214 |
| 2008/0103366 A1* | 5/2008 | Banchieri | A61B 1/32 600/208 |
| 2008/0154351 A1* | 6/2008 | Leewood | A61F 2/86 623/1.2 |
| 2008/0300665 A1 | 12/2008 | Lootz et al. | |
| 2009/0088604 A1 | 4/2009 | Lowry et al. | |
| 2009/0143861 A1 | 6/2009 | Errico et al. | |
| 2009/0222044 A1* | 9/2009 | Gorek | A61B 17/0218 606/279 |
| 2010/0312189 A1 | 12/2010 | Shelton et al. | |
| 2011/0040366 A1 | 2/2011 | Goetz et al. | |
| 2011/0144687 A1 | 6/2011 | Kleiner | |
| 2012/0088979 A1* | 4/2012 | Nunley | A61B 17/025 600/231 |
| 2013/0090527 A1* | 4/2013 | Axon | A61B 1/00075 600/114 |
| 2016/0213500 A1* | 7/2016 | Beger | A61B 17/025 |
| 2016/0346084 A1 | 12/2016 | Taylor et al. | |
| 2018/0280014 A1* | 10/2018 | Beger | A61F 2/90 |

FOREIGN PATENT DOCUMENTS

| | | |
|---|---|---|
| DE | 102015100932 A1 | 7/2016 |
| WO | 9937245 A1 | 7/1999 |
| WO | 2016007412 A1 | 1/2016 |

OTHER PUBLICATIONS

Extended European Search Report for European Application No. 18 164 843.7, dated Jan. 4, 2019, with translation—29 pages.
German Search Report for German Application No. 10 2017 106 846.5, dated Jan. 16, 2018, with partial translation, 17 pages.
German Standard, Medical Instruments, Retractors Type Langenbeck, with English translation, Feb. 2010, 12 pages.

* cited by examiner

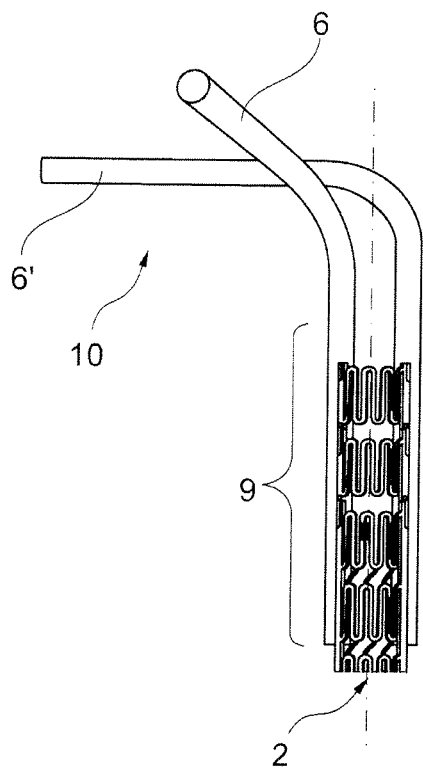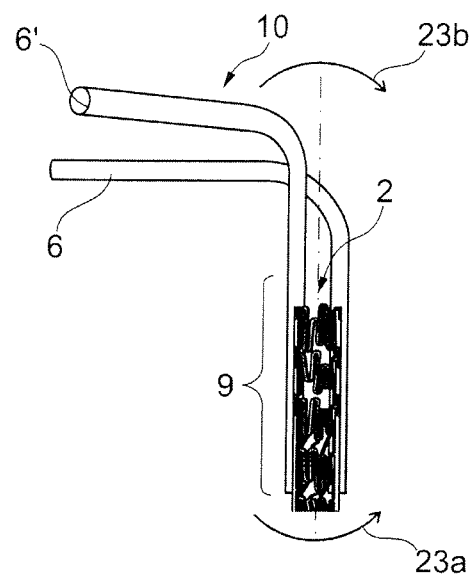
Fig. 3a  Fig. 3b
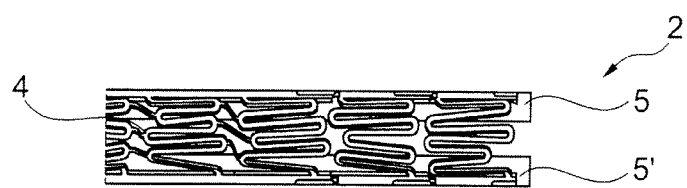
Fig. 4

SURGICAL RETRACTOR SYSTEM COMPRISING A RETRACTOR AND AN EXTRACTOR AS WELL AS A SURGICAL INSTRUMENT APPLYING A TORSIONAL LOAD

RELATED APPLICATION(S)

This application is related to and claims the benefit of priority of German Application No. 10 2017 106 846.5, filed Mar. 30, 2017, the content of which is incorporated by reference herein in its entirety.

FIELD

The present disclosure relates generally to a surgical retractor system, and more specifically to a retractor system having a retractor and an extractor. The retractor can be designed as a stent and additionally prepared to perform a distractor function. The disclosure also relates to a surgical instrument for releasing a distractor and/or a retractor. A surgical instrument of this type may also be referred to as an extractor unit.

BACKGROUND

A surgical retractor system comprising a retractor and an extractor is first of all able to keep an operating field/an incision open. For this purpose, the retractor is inserted into the surgical field from outside of a patient to be treated and spreader elements/expanding sections formed by the retractor are spaced apart. This causes the connective and/or muscle tissue to be pushed apart, thus expanding the surgical field. Secondly, the at least one extractor of the surgical retractor system or the surgical system is designed to compress the force-operated spreader elements at the end of an operation or operation step again in order to enable the retractor to be released from the patient.

A distractor, on the other hand, is generally a surgical instrument or device for the controlled spreading/pulling apart of body structures by mechanical action from outside (distraction). Distractors are used for example in trauma surgery, orthopedics and jaw surgery for the extension treatment of bones.

Prior art retractors are known to perform a distractor function in addition to the retractor function. German application no. 10 2015 100932 A1, which is incorporated by reference herein in its entirety, discloses a stent retractor/distractor, i.e. a retractor with a stent structure. This has a radially flexible, expandable tubular jacket, which is divided in circumferential direction into at least two sections, namely a stiffening section and an expansion section with differing radial flexibility, which are connected to each other in a one-piece material bond. This enables the stent retractor/distractor to be adapted to a patient-side opening.

As an extractor, i.e. the instrument for removing/releasing the stent retractor/distractor from the patient-side opening, a compression forceps is disclosed in the above-mentioned application. This compresses the stent retractor/distractor until it is detachable. Compression forceps are usually present in operating rooms and undergo a complex disinfection cycle after each use.

The disadvantage of this prior art is firstly that the destructive effect of the compression forceps on the stent retractor/distractor varies from case to case, which often results in a time-consuming and unpredictable process of releasing the retractor from the patient-side opening. Furthermore, the use of the compression forceps results in a costly and time-consuming disinfection process after each use, which impairs the efficiency of the retractor system.

Last but not least, prior art technology involves that the prerequisites for an intra-operative removal of the retractor, i.e. during surgery, are so unfavorable that additional time and instruments have to be planned in order to ensure a scheduled procedure.

SUMMARY

In view of the above-mentioned prior art, it is the object of the present disclosure to eliminate the disadvantages from prior art and, in particular, to disclose a surgical retractor system that enables efficient release/removal of the retractor, for example from the patient-side opening. The main focus here is on the defined deformation of the retractor by the extractor, which offers the prospect of a reliable and time-efficient detachment.

Furthermore, one of the primary aims of the present disclosure is to reduce the logistical effort required to keep the surgical retractor system in the operational state. In addition, the risk of injury caused by deformed retractors, preferably made of metal sheets, is also to be minimized.

A further object of the disclosure is to provide a retractor or surgical instrument that can be produced cheaply and is easy to disinfect, which is robust in use and virtually eliminates operating errors.

The abovementioned objects and aims are achieved/solved according to the disclosure by means of a surgical retractor system and by means of a surgical instrument described herein.

From this design, according to the disclosure, of the surgical retractor system and the surgical instrument, the following additional advantages can be derived, for example:

- A defined destruction of the disposable/single-use retractor allows the intra-operative removal of the retractor without complications.
- The plate section of the retractor, which is prepared for interaction with the retractor, provides safe access for the extractor, thus increasing the safety of the retractor system.
- The extractor is designed to match the corresponding plate section, which requires less flexibility in operation, resulting in cheaper components.
- The more economical production of the extractor makes it possible to design it as a disposable component, which makes it possible to implement a so-called single-use concept.
- Thanks to the single-use concept, the retractor system can also be used in places/clinics/health centers where there are no economically viable sterilization options.
- The sterilization process costs can be reduced due to the single-use concept.
- The pre-defined point of contact for the extractor at the plate section of the retractor prevents burrs/cutting edges from occurring on the plastically deformed extractor, which increases not only the safety of the patient but also that of the operating staff.
- The retractor can be bent/deformed with a minimum of effort due to an efficiently designed interaction between the handle section and the operating section of the extractor unit/surgical instrument.

A Poka-Yoke principle is implemented via a slotted arrangement in the operating section, which prevents incorrect operation of the surgical instrument by a user, such as a surgeon.

Therefore, the subject-matter of the disclosure is, for one thing, a surgical retractor system with an essentially tubular retractor, which preferably has several segments in the axial direction. These can be irreversibly separated from each other in order to adjust the length of the retractor so that the latter can be flexibly designed in its longitudinal direction. At least one of the segments is further preferentially subdivided in circumferential direction into at least one expanding section/spreading element and one plate section/extractor engagement section. These two sections have different radial flexibilities and are preferably joined together in a one-piece material bond so that a plastic radial expansion of the retractor is possible. As mentioned above, said radial expansion of the retractor serves, on the one hand, to keep the operating field open. On the other hand, the distraction that can be carried out by the retractor according to the disclosure can also be realized. The surgical retractor system also has at least one extractor/compression instrument/compression tool/compression mechanism, which can be actuated in such a way that it causes plastic radial constriction of the retractor in opposition to the radial widening of the retractor. This radial constriction causes the destruction of the retractor and allows it to be removed from the opening.

According to the disclosure, the at least one extractor is prepared to cooperate with the retractor, preferably with its at least one plate section, for the introduction of a torsional moment in order to achieve the radial constriction of the retractor. There is thus a kind of matrix-patrix relationship between the retractor-side plate section and the extractor. If the geometry of the plate section is changed, the extractor must also be adapted to this change. This interaction of the two components of the retractor system ensures time-efficient deformation of the retractor, which allows an intraoperative removal of the retractor.

In an advantageous embodiment, the extractor is prepared to enforce the plastic radial contraction of the retractor by means of a torsional moment acting on the retractor. For one thing, the torsional moment causes a kind of winding up the retractor on the extractor, which results in a reliable radial/diameter constriction. Secondly, the torsion-based deformation according to the disclosure can be realized by means of a form-fit connection between the extractor and the retractor. Since sufficient rigidity is ensured for the respective components, it is not possible to unintentionally release the form fit. This increases the safety of the retractor system, since it is impossible for the tool to slip off, as is often the case with prior art compression forceps.

In particular, if the extractor has a handle section and an operating section with a slit, which can be mounted on the plate section of the retractor in such a way that it encompasses the retractor on its radially inward facing surface and on its radially outward facing surface, the reliability of the positive fit is increased.

In another embodiment according to the disclosure, a second extractor is prepared to cooperate with a second plate section of the same retractor in such a way that two extractors cause a radial constriction of the one retractor. The use of a second extractor makes it possible to produce a comfortable deformation with two hands. The second extractor should preferably have the same design as the first extractor. This reduces production costs. In addition, the second extractor allows the realization of the extractor with a simple geometry (since two extractors with a simple geometry produce the same effect as one extractor with a complex geometry). Production costs are thus further reduced, which makes it possible to implement not only the retractor but also the extractor and thus the entire retractor system as a disposable/one-way product in accordance with the single-use concept.

In an advantageous embodiment, the surgical retractor system is characterized in that the two extractors are prepared to force the retractor onto the extractors by winding/rolling/twisting/bending by means of opposite twisting movements. For example, when the retractor is subjected to an opposite rotational movement, a torsional moment similar in function to that of a sardine can is produced.

It is particularly advantageous if a predetermined breaking point is arranged in the axial direction along the plate section of a segment of the retractor in order to cause a buckling of the retractor at the predetermined breaking point when the torsional moment is applied. This guarantees that the retractor follows a predetermined buckling/break line. Alternatively, the inventive concept also includes the idea that the predetermined breaking point extends at an angle to the axial direction in order to cause a fan-like radial constriction. Such a predetermined breaking point increases the operating safety first of all, since the corresponding breaking edges are round in shape, and secondly it enables the treating surgeon to achieve a comfortable radial constriction. In the prior art, the tedious dragging of the retractor is thus avoided.

In a further aspect of the disclosure, a surgical instrument for releasing a distractor or also a retractor from an opening, preferably a patient-side opening, held open by the distractor/retractor is described. The surgical instrument, which can also be referred to as an extractor unit, has at least one handle section defining a longitudinal axis of the handle and at least one operating section defining a longitudinal effective axis, which are coupled with each other via a connecting section/connecting link. In accordance with the disclosure, the connecting section arranges the handle section and the operating section relative to one another such that the handle's longitudinal axis and the longitudinal effective axis are angled relative to each other, preferably at an angle between 60° and 140°, preferably 90°. The angle between the handle's longitudinal axis and the longitudinal effective axis is described here as moving from the longitudinal effective axis in the direction of the handle's longitudinal axis. At an angle of 60°, the connecting section therefore defines a sharp angle.

In particular, if the handle section of the surgical instrument has a substantially circular and essentially constant cross-section over the entire length along the handle's longitudinal axis and the operating section has a substantially circular and essentially constant cross-section over the entire length along the longitudinal effective axis, the aim of favorable manufacturing costs can be achieved, whereby a single-use concept becomes feasible. Preferably, the diameter of the handle section corresponds to the diameter of the operating section. Deviations of up to 10% of the diameters from each other are also covered by the inventive idea.

The surgical instrument preferably has a longitudinal slit preferably at its operating section, which extends along the longitudinal effective axis and divides the operating section into two circumferentially separated legs, which are of the same or at least similar size in terms of their size, i.e. the area occupied in the cross-section. The length and the cross-sectional area of the legs are essentially the same. In other words, the longitudinal slit extends in a plane in which the longitudinal effective axis extends as well.

As soon as the first leg of the operating section is prepared to contact the retractor from radially outside/laterally and the other, second leg of the operating section is prepared to contact the retractor from radially inside/medially, an efficient, error-free positioning of the extractor unit on the retractor is guaranteed.

It is particularly preferred that the surgical instrument is composed of two identical angled extractors, which increases comfort and operating accuracy, since the plastic deformation of the retractor caused by the surgical instrument can be initiated by both hands of a surgeon, which means that less force may be applied by the individual hand. This also increases the precision of the surgical instrument.

Another advantageous embodiment is distinguished in that the length of the connecting section is small in relation to the length of its angled course, i.e. the amount of the length of the connecting section if it were "bent straight", is small compared to the length of the operating section along the longitudinal effective axis and the length of the handle section along the handle's longitudinal axis. Thus, a robust arrangement without superfluous component sections is achieved, since the handle section and the operating section represent the majority of the surgical instrument and, for example, no material and/or installation space has to be applied for hinges or joints.

Preferably, the at least one extractor or the surgical instrument is based on a blank having a cross-section which is preferably realized as a round, solid profile bar or hollow profile bar whose connecting section is formed by forming work, in particular bending the bar, and whose operating section comprises at least one longitudinal slit manufactured by a chipping production step such as sawing or grinding, or by a stamping or laser step, said longitudinal slit dividing the distal bar end in the area of the operating section in at least two legs which preferably have the same size, whereby the surgical instrument is suitable as a disposable component. In this way, a simple geometry is achieved with economically producible components that are so inexpensive to purchase that they can be used as disposable products/one-way products/single-use products without the need for a disinfection process.

In particular, if the expanding section is designed like a stent/so as to have a stent structure to enable plastic deformation in radial direction, advantages in handling the retractor system are offered.

Furthermore, an advantageous embodiment aims to design the at least one extractor as a disposable component in order to avoid a disinfection process.

In other words, the disclosure can be described in such a way that two slotted extractors can be mounted on the plate sections from outside and in a distally form-fitting manner, while said plate sections give stiffness to the radially flexible retractor. Having placed the two extractors, it is possible to twist the two extractors against each other in such a way that they deform the retractor, which rotates with the rotation of the extractor due to the positive fit, and reduce its diameter so that it is easily detachable from its position.

It is also possible to place the at least one extractor on the retractor in such a way that a tractive force can also be transferred to it. Preferably, the tensile force should be combined in series with the torsional moment, in order to first produce a tube shape from an approximate funnel shape of the retractor by means of the tensile force, before it is rolled up by means of the torsional moment.

According to another aspect of the present disclosure, a retractor system comprising a retractor stent, i.e. a retractor with a stent structure, is proposed which is adapted for being used as a retractor. Due to the inventive dividing of the wall structure into sections with higher and lower flexibility, the retractor stent has on the one hand the property of being deformable in any radial direction (e.g. round, oval, etc.), while at the same time it maintains a sufficient stiffness to keep the tissue in a spread-apart state. For example, a minimally invasive access can be created in the form of a lumbar, thoracic and/or cervical spinal access. Cranial applications are also possible.

The expanding sections serve to change the diameter of the retractor stent, whereas the plate sections/stiffening sections increase the stability of the stent against external radial forces at least in certain radial directions and at the same time provide a defined contact surface for the extractor. This makes it possible to use the retractor stent as an alternative or in addition to its retraction function as a distractor instrument, since its resistance to radial compression forces, which can be achieved in principle via the stiffening sections, is sufficient to keep bones apart.

The design of the retractor stent, preferably in the form of a one-piece material bond, makes it possible to produce the stent quickly and easily, for example by laser or water cutting of metal sheets.

Furthermore, the wall structure (shell) of the retractor stent is preferably subdivided into circumferential direction into four sections, two of which are designed with essentially the same flexibility as plate sections/stiffening sections and the other two are designed as expansion sections with essentially the same flexibility, for which the two plate sections/stiffening sections have a higher stiffness than the two expansion sections, at least in circumferential direction and preferably also in axial direction. Due to this further development, the retractor stent can be expanded by simple ways and means such as a dilatation balloon, a speculum or a Langenbeck hook, preferably evenly (symmetrically) or also in oval shape. For this purpose in particular, the two sections can also be arranged diametrically opposite each other with equal flexibility.

It is also advantageous if the segments of the retractor stent are coupled to each other via axial connecting elements/bars with preferably higher stiffness, which form predetermined breaking points for segmental length shortening. This design ensures that the retractor stent substantially expands only radially under internal pressure load. In addition, the length of the stent can be easily adapted to suit its intended location in the patient's body.

In principle, the function of the extractor according to the disclosure follows the function of an opening device of a generally known food can. Sometimes a winding rod is used there, which has a longitudinal slit in which a tab on a can lid to be removed can be inserted. As soon as the winding rod is then turned around its longitudinal axis by a handle formed on it, the can lid is wound onto the winding rod and thus exposes the can access.

The present disclosure makes use of this principle by means of which the extractor/extractor unit/surgical instrument according to the disclosure has at least one such winding rod as an extractor with a handle (section) or lever formed on it, which can be brought into a (linear) form-fit with the tubular/sleeve-shaped retractor/stent or its wall in such a way (e.g., by means of a longitudinal slit on the winding rod or a radially protruding driving pin) to transfer a torque applied to the winding rod via the lever around its longitudinal axis to the wall of the retractor/stent and thus to cause a buckling and winding of the wall in the longitudinal direction of the retractor.

If two such rewinding rods/extractors are preferably provided, they can, for example, have a form-fitting engagement at diametrically opposed angular positions on the wall of the retractor/stent and cause a symmetrical winding of the wall at the corresponding two positions.

Insofar as the two winding rods are (centrally) connected to each other in a hinge-like manner and coupled so as to be freely rotatable around their longitudinal axis (to form an extractor unit in this way), the winding rods can also be spread apart in scissor-like manner at their handles/levers, so that the retractor/stent can be radially expanded by means of the extractor unit according to the disclosure.

BRIEF DESCRIPTION OF THE DRAWING FIGURE(S)

Figure 2:
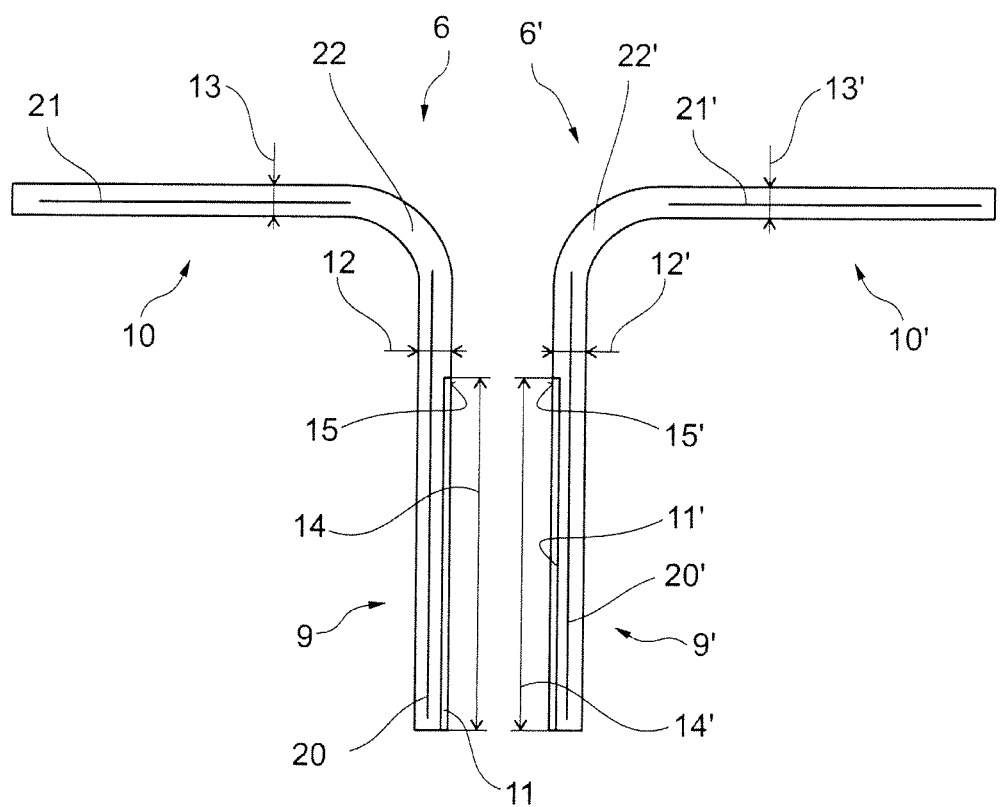
Figure 5:
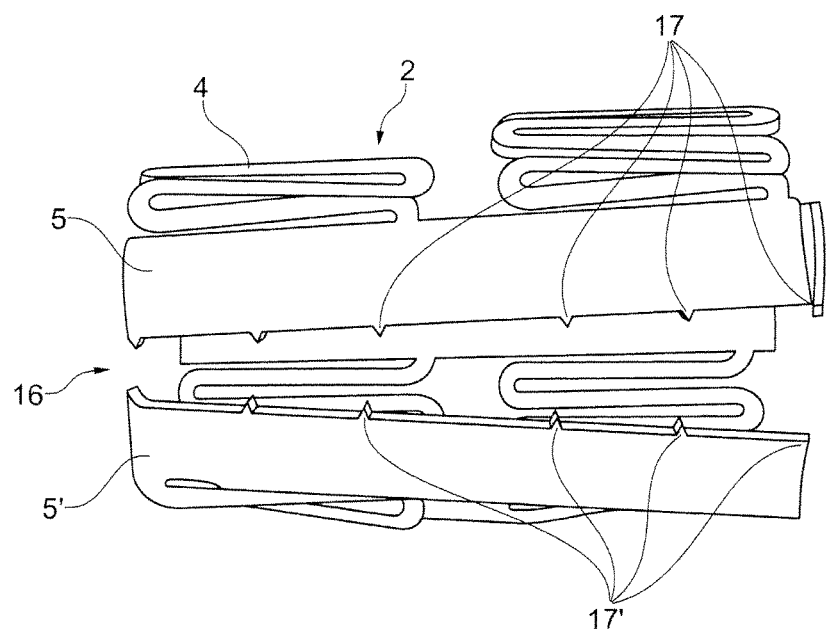

The disclosure will be explained in more detail below on the basis of preferred exemplary embodiments with reference to the accompanying Figures. The Figures are of schematic nature only and exclusively help to understand the disclosure. The same elements are provided with identical reference numerals. In the Figures:

FIG. 1: is a schematic view of a retractor system according to the disclosure in a first embodiment in which an extractor cooperates with a plate section;

FIG. 2: shows two extractors according to the disclosure in a first embodiment;

FIG. 3a: shows the retractor system in which one retractor of the two extractors is subjected to a torsional load;

FIG. 3b: shows the retractor system in which one retractor of the two extractors is subjected to a torsional load;

FIG. 4: shows a retractor which has been plastically deformed by the extractor, illustrated on its own; and FIG. 5: shows a retractor in a further embodiment comprising a predetermined breaking point.

DETAILED DESCRIPTION

FIG. 1 shows a surgical retractor system 1 comprising one retractor 2 and two extractors 6, 6', which can also be seen as an extractor unit 6, 6' or basically as a surgical instrument. From the extractors 6, 6', only an operating section 9 is illustrated, i.e. the winding rod. Regarding a handle section 10 of the extractors 6, 6', reference is made to FIG. 2.

The retractor 2 is subdivided into a plurality of segments 3, 3', 3'', 3''' in the longitudinal direction/axial direction which is indicated by arrow 7. The respective segments 3, 3', 3'', 3''' are designed so as to have the same structure. Immediately upon inserting the retractor 2 in a patient-side opening, the segment-type design allows the individual segments 3, 3', 3'', 3''' to be severed from each other in axial direction, realizing a length adaptation of the retractor 2.

In the circumferential direction indicated in FIG. 1 with arrow 8, each segment 3, 3', 3'', 3''' of the retractor 2 can be subdivided into two expanding sections/spreading sections 4 in each case, from which only one can be seen in the view of FIG. 1, and into two plate sections 5, 5'. The expanding section 4 and the plate section 5, 5' are of different radial flexibility. Thus, the expanding section 4 can be plastically deformed owing to a stent-like structure which in the present example is formed as a wave shape with a high amplitude as compared to its frequency, allowing a radial expansion of the diameter of the tubular retractor 2. The expanding sections 4 and the plate sections 5, 5' are arranged to be diametrically opposite each other, resulting in an alternating arrangement of the different portions.

Apart from the radial flexibility which is ensured substantially by the expanding sections 4, the retractor system 1 according to the disclosure provides for sufficient robustness of the retractor 2. This robustness is required, on the one hand, to realize the initially mentioned distractor function of the retractor 2 and, on the other hand, to form a point of attachment/coupling place for the extractors 6, 6'.

The extractors 6, 6' are tools/instruments/a surgical instrument mainly for removing/detaching the retractor 2 from a patient-side opening. When operated by a surgeon, they bring about a radial constriction by means of a plastic deformation of the retractor 2, which ends the state of keeping open/spreading apart caused by the retractor 2 prior to this and allows an intra-operative removal of the retractor 2. By means of a longitudinal slit 11, 11' presented in more detail in connection with FIG. 2, the extractors 6, 6' are attached on the retractor 2 to be detached in such a manner that a first leg 18, 18', which is clearly visible in FIG. 1, contacts the retractor 2 from radially inside/medially, whereas a second leg 19, 19' contacts the retractor from radially outside/laterally. These two legs 18, 18', 19, 19' allow to realize the winding function, according to the disclosure, of the winding rod/operating section 9, 9'.

For the purpose of permitting the plastic deformation by the extractors 6, 6' in a reliable and predictable manner, a predefined active or effective surface of the extractors 6, 6' on the retractor 2 form part of the inventive idea. This active surface is ensured by the plate sections 5, 5' which have sufficient stiffness to transmit any torsional load—which in this exemplary embodiment is introduced from the extractors 6, 6' into the retractor 2 and its wall—to the expanding sections 4 such that the retractor 2 is plastically narrowed in radial direction.

FIG. 2 illustrates the extractors 6, 6' from FIG. 1 on their own. The above-mentioned operating section/winding rod 9 of the extractor 6 and the operating section/winding rod 9' of the extractor 6' extend at an angle of about 90° from the handle section 10, 10' which forms a lever in the present case. The value of 90° relates to the angle between a longitudinal effective axis 20, 20' representing the longitudinal axis of the operating section 9, 9', and a handle's longitudinal axis 21, 21' which by analogy represents the longitudinal axis of the handle section 10, 10'. The illustrated angle of 90° is not to be understood in a limiting sense. Rather, angle ranges between 60° and 140° can be realized according to the disclosure. The intermediate portion between the operating section 9, 9' and the handle section 10, 10' is implemented by a connecting section 22, 22'. The connecting section 22, 22' is realized preferably by a forming process. Hence, the surgical instrument/the extractor 6 in the unprocessed state is a bar having a uniform diameter, which is first deformed in the area of the connecting section 22, 22' by the desired angular range, which may be carried out before or alternatively after the longitudinal slit is/has been machined in the operating section 9, 9'. Regarding the length along its bent longitudinal axis, the connecting section 22, 22' is small as compared to the operating section 9, 9' and the handle section 10, 10'.

The longitudinal slit 11, 11' preferably extends through the cross-sectional center of the operating section 9, 9'. The slit 11, 11' is dimensioned such that it can be turned over/placed on the plate section 5, 5' in the longitudinal direction of the retractor/stent. In other words, the width of the slit on the extractor 6, 6' allows to insert the retractor wall in the longitudinal direction of the retractor 7. As seen in the circumferential direction, the retractor wall is preferably composed of the at least one expanding section 4 and the at least one plate section 5, 5'. Hence, a form-fitting connection is produced between the retractor 2 and the extractor 6, 6' in the circumferential direction 8 of the extractor, which in turn brings about a buckling and coiling of the retractor wall (with a large transmission ratio or leverage) upon rotating the extractor 6, 6' around its longitudinal axis, efficiently allowing the radial constriction. Said form-fitting connection is made possible by the two legs 18, 19 presented in connection with FIG. 1 and defining the slit 11.

The diameter 12, 12' of the operating section 9, 9' preferably corresponds substantially to the diameter 13, 13' of the handle section 10, 10' and is much smaller compared with the diameter of the retractor/stent. The uniformity of the diameter results from the fact that the extractor 6 in the unprocessed state preferably is a bar, as described above. The handle section 10, 10' further does not comprise any ergonomic specifics. This means that the extractor 6, 6' is an uncomplicated bar component which can be produced in an economical way, allowing the surgical retractor system 1 to be realized as a single-use concept.

The slit length 14, 14' of the slit 11, 11' is prepared to exceed the length of at least three segments 3, 3', 3" in the axial direction 7. This ensures the possibility to transmit a sufficiently high force and moment from the extractor 6, 6' to the retractor 2 and the wall thereof. A slit base 15, 15' of the slit 11, 11' is designed such that it represents a stop for the one (proximal) end face of the retractor 2. This means that the axial placement of the extractor 6, 6' on the retractor 2 or its wall can be realized in a predefined manner by means of the slit width cooperating with the plate section 4, on the one hand, and by the slit base 15, 15', on the other hand.

FIGS. 3a and 3b illustrate the retractor's 2 radial constriction caused by the extractors 6, 6'. In these two Figures, a relative rotation of the two extractors 6, 6' relative to each other has taken place around their respective longitudinal axes, resulting in a plastic deformation in the form of a radial constriction of the retractor. The retractor 2 has been acted upon with a torsional moment by the extractors 6, 6', resulting in a coiling/winding/twisting/"crumpling" of the retractor 2 and its wall. The torsional moment is indicated with the two arrows 23a and 23b, implementing an opposite rotation and hence a torsion around the longitudinal axis of the retractor 2, which from perspective reasons is not readily apparent from the schematic diagram in FIG. 3b. Whereas the distal portion of the retractor 2, such as through its anchoring in the patient-side opening, is subjected to a moment in the first direction (23a), the proximal portion of the retractor is acted upon with a moment by the extractor 6, 6' in the second, other direction (23b). This results in the radial constriction, according to the disclosure, of the retractor 2.

FIG. 4 illustrates the retractor 2 in the radially narrowed state. Thus, it has been plastically deformed by the extractors in FIG. 3a, 3b such that the plate sections 5, 5' rest against each other. The expanding sections 4 have been deformed as well. The rolled/wound retractor illustrated in FIG. 4 can be easily taken out from a patient-side opening.

FIG. 5 shows a retractor 2 in a further embodiment. A predetermined breaking point 16 is provided between the plate sections 5, 5'. In the state illustrated in FIG. 5, it has already been severed. The predetermined breaking point 16 is realized by means of individual protrusions 17, 17' which are formed from the respective plate section 5, 5'. In the (non-illustrated) state in which the predetermined breaking point 16 is not yet severed, the protrusions 17, 17' arranged at the same level have a material bond contact in each case. The retractor of FIG. 5 has already been deformed by extractors 6, 6' which are not illustrated here, indicated by the severed predetermined breaking point 16.

In the following, the structure of the retractor 2 will be explained again in particular with reference to FIG. 1. As seen in the circumferential direction, the wall structure thereof consists of two circumferential portions with low rigidity 4 and two circumferential portions with a comparably high rigidity 5, 5', which alternate in the circumferential direction and are linearly arranged in the axial direction 7.

Basically, the retractor 2 according to the disclosure has the shape of a tube or hose, wherein the circumferential portions with identical/similar rigidities lie diametrically opposite each other. The retractor 2 is further designed in the form of a one-piece material connection, i.e. the individual circumferential portions are connected to one another in a one-piece material bond.

The retractor 2 substantially has a wall structure which has been adopted in principle from a standardized vessel stent (such as the stent Coroflex by Aesculap AG). This means that the retractor 2 at least in the area of its expanding sections (widening elements) 4 is formed from a number of axially spaced, preferably parallel strips which extend in a serpentine- or concertina-like manner in the circumferential direction and in this way form flexible means capable of radially expanding in the area of their concertina shape.

For the purpose of enhancing the stability, the stiffer transition portions (stiffening portions/plate sections) 5, 5' are each (alternatingly) arranged between the two expanding sections 4 as seen in the circumferential direction. The stiffening portions (stiffening elements) 5, 5' are formed by substantially closed, preferably rectangular plate sections which in their basic shape as seen in axial direction are curved like a tub or trough and provided to not expand radially or only to a slight extent. The stiffening portions 5, 5' are also used to form an attachment point for the extractor 6, 6'. The aim is to provide the geometry of the wall structure with as many functionalities as possible.

The material for the retractor 2 according to the disclosure may be steel, titanium or plastics, wherein a plastic part is preferably formed in injection-molding technology. Further, the retractor 2 after cutting the wall profiles may be deburred by electro-polishing, for instance. In order to improve the reflection characteristics in terms of lighting technology, for example in microscope applications, the surface of the remaining structure may also be matte-finished or coated.

The invention claimed is:

1. A surgical retractor system comprising: a substantially tubular retractor having, in an axial direction, a number of segments which can be irreversibly severed from one another in order to carry out a length adaptation of the retractor, at least one segment being subdivided in a circumferential direction into at least one expanding section and at least one plate section which are of differing radial flexibility and connected to each other in a one-piece material bond so that a plastic radial expansion of the retractor is made possible, and comprising a first extractor which is configured such that it brings about upon its actuation a plastic radial constriction of the retractor contrary to the radial expansion of the retractor, wherein the first extractor is prepared and arranged in such a manner to cooperate with the at least one plate section for introduction of a torsional moment in order to effect the radial constriction of the retractor.

2. The surgical retractor system according to claim 1, wherein the first extractor is prepared and arranged in such a manner to forcibly cause the plastic radial constriction of the retractor by a torsional moment acting on the retractor to bring about a buckling of a retractor wall in a longitudinal direction of the retractor.

3. The surgical retractor system according to claim 2, wherein a predetermined breaking point is arranged in the axial direction along the at least one plate section of the at least one segment of the retractor to bring about a buckling of the retractor at the predetermined breaking point when acted upon with the torsional moment.

4. The surgical retractor system according to claim 1, wherein the first extractor comprises a handle section, a first section, and a second section, the first section having a longitudinal slit, which can be attached to the at least one plate section such that it encompasses the latter at a surface pointing radially inwards and a surface pointing radially outwards in a quasi linear manner.

5. The surgical retractor system according to claim 4, wherein at least the first extractor is based on a blank having a cross-section which is a round, solid profile bar or hollow profile bar, the second section being formed by forming work, and the first section comprising at least one longitudinal slit dividing a distal bar end in at least two legs which have the same size, whereby the surgical instrument is suitable as a disposable component.

6. The surgical retractor system according to claim 1, further comprising a second extractor, the second extractor prepared and arranged in such a manner to cooperate with a second plate section of the first extractor in such a manner that the first and second extractors bring about a radial constriction of the retractor.

7. The surgical retractor system according to claim 6, wherein the first and second extractors are prepared and arranged in such a manner to forcibly cause the retractor to be wound up on the first and second extractors by opposite rotary movements.

8. The surgical retractor system according to claim 1, wherein the at least one expanding section is designed like a stent to allow for plastic deformation.

9. A method for releasing or removing the retractor in the surgical retractor system according to claim 1, comprising the steps of:
  preparing and arranging the first extractor to cooperate with the at least one plate section of the at least one segment in the retractor; and
  introducing the torsional moment upon actuation of the first extractor to effect the radial constriction of the retractor.

* * * * *